United States Patent
Parker et al.

(10) Patent No.: US 6,990,365 B1
(45) Date of Patent: Jan. 24, 2006

(54) APPARATUS FOR MEASUREMENT OF BLOOD ANALYTES

(75) Inventors: Dawood Parker, Whitland (GB); David Keith Harrison, Durham (GB)

(73) Assignee: Edwards Lifesciences, Irvine, CA (US)

(*) Notice: Subject to any disclaimer, the term of this patent is extended or adjusted under 35 U.S.C. 154(b) by 0 days.

(21) Appl. No.: 09/743,206

(22) PCT Filed: Jul. 2, 1999

(86) PCT No.: PCT/GB99/02127
§ 371 (c)(1), (2), (4) Date: Mar. 15, 2002

(87) PCT Pub. No.: WO00/01294
PCT Pub. Date: Jan. 13, 2000

(30) Foreign Application Priority Data

| Jul. 4, 1998 | (GB) | 9814464 |
| Nov. 13, 1998 | (GB) | 9824899 |
| Nov. 19, 1998 | (GB) | 9825243 |

(51) Int. Cl.
*A61B 5/00* (2006.01)

(52) U.S. Cl. .................. 600/328; 600/322
(58) Field of Classification Search ......... 600/322–323, 600/326, 316, 349, 328, 344
See application file for complete search history.

(56) References Cited

U.S. PATENT DOCUMENTS

| 4,407,290 A | * | 10/1983 | Wilber ............... 600/330 |
| 4,752,115 A | * | 6/1988 | Murray et al. ....... 600/321 |
| 5,040,539 A | * | 8/1991 | Schmitt et al. ...... 600/340 |
| 5,673,692 A | * | 10/1997 | Schulze et al. ...... 356/41 |
| 5,755,226 A | * | 5/1998 | Carim et al. ........ 600/323 |
| 5,879,294 A | * | 3/1999 | Anderson et al. .... 600/310 |
| 6,045,502 A | * | 4/2000 | Eppstein et al. ..... 600/306 |
| 6,049,727 A | * | 4/2000 | Crothall ............. 600/310 |
| 6,064,896 A | * | 5/2000 | Rosenthal ........... 600/316 |
| 6,078,833 A | * | 6/2000 | Hueber .............. 600/310 |
| 6,097,975 A | * | 8/2000 | Petrovsky et al. .... 600/316 |

* cited by examiner

*Primary Examiner*—Eric F. Winakur
*Assistant Examiner*—Matthew Kremer
(74) *Attorney, Agent, or Firm*—Edwin D. Schindler; Debra Condino; Theodore Lopez

(57) ABSTRACT

There is described a device for the non-invasive measurement of one or more analytes in blood in a patient's body part which comprises a light transmitter comprising a plurality of transmitting fibres positioned to transmit light to the body part and a light detector comprising a plurality of light detector fibres position to detect light transmitted through or reflected from the body part. The device especially utilises the non-pulsatile element of a patient's blood. There is also described a method of measuring blood glucose levels and a device programmed so as to calculate one or more of the haemoglobin index, the oxygen index and the blood oxygen saturation.

23 Claims, 2 Drawing Sheets

Figure 1:
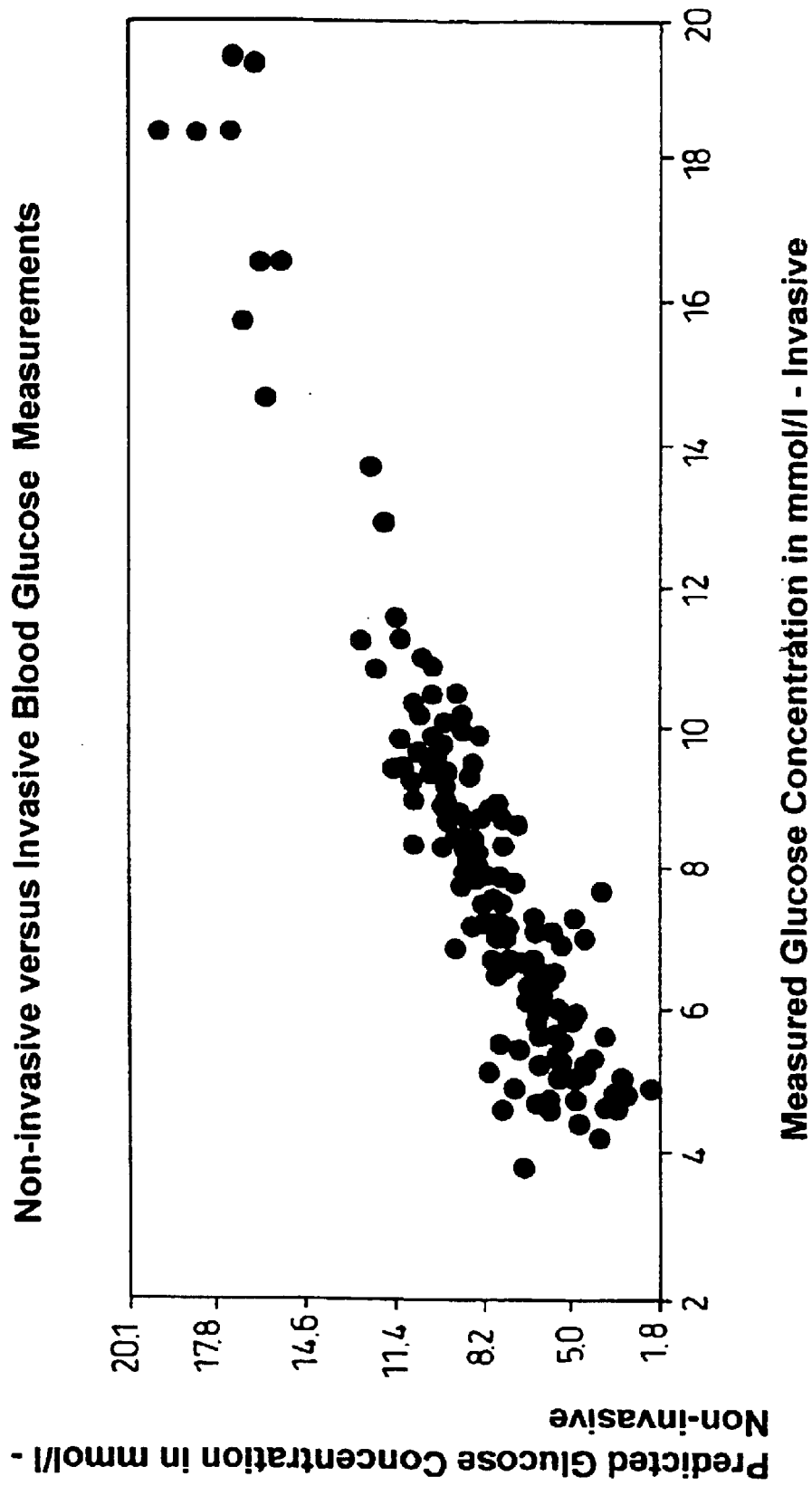

An example of blood glucose levels during the day

APPARATUS FOR MEASUREMENT OF BLOOD ANALYTES

BACKGROUND OF THE INVENTION

1. Technical Field of the Invention

This invention relates to a novel monitor, particularly a monitor for the non-invasive measurement of glucose in eg diabetics and a method for determining glucose levels.

Diabetes mellitus (abbreviated to diabetes) is the name for a group of chronic or lifelong diseases that affect the way the body uses food to make energy necessary for life. Primarily, diabetes is a disruption of carbohydrate (sugar and starch) metabolism and also affects fats and proteins. In people who have diabetes the glucose levels vary considerably being as high as 40 mmol/l and as low as 2 mmol/l. Blood glucose levels in people without diabetes vary very little, staying between 3 and 7 mmol/l. These levels follow the typical patterns shown in FIG. 1a.

2. Description of the Prior Art

Hyperglycaemia (high blood glucose)

Both insulin dependant diabetes (IDDM) and non-insulin dependant diabetes (NIDDM) are associated with serious tissue complications which characteristically develop after 10–20 years duration of diabetes. Diabetic eye disease, retinopathy, is the commonest cause of blindness in western countries in people under the age of 65 years. Diabetic renal disease, nephropathy, is an important cause of kidney failure in the community. Diabetic neuropathy affects the peripheral nerves causing impaired sensation and leg ulcers, and damage to the autonomic nervous system causes postural hypertension (low blood pressure on standing) and diarrhoea. Atherosclerosis is 2–4 times as high in diabetic as non-diabetic people and manifest as an increased frequency of myocardial infarction (heart attacks), cerebrovascular disease (strokes) and the peripheral vascular disease (causing reduced circulation to the limbs and the risk of gangrene and amputation).

For many years it has been something of an article of faith in clinical diabetes that the cause of the complications in exposure of the tissues over many years to the higher than normal blood glucose levels which have been usual in most treated diabetic patients. Conclusive proof of this theory has only recently become available; the landmark Diabetes Control and Complications Trial (DCCT) in North America was announced in 1993 and showed that IDDM patients randomly assigned to an intensive and optimised insulin treatment programme designed to produce near-normal blood glucose levels had significantly less retinopathy, kidney disease and neuropathy over a 9-year period that patients assigned to ordinary treatment (ie poor control).

The DCCT has been a major stimulus to physicians around the world to renew efforts to improve control in diabetic patients, and to develop improved methods of obtaining good control and of monitoring these patients.
Hypoglycaemia (low blood glucose)

An important additional finding in the DCCT was that the frequency of hypoglycaemia was three-fold higher in the well-controlled patients that those with ordinary control. This confirms the long-standing appreciation by physicians that hypoglycaemia is extremely frequent in IDDM, and especially so in those that are well controlled. There are many reasons for this including mistiming of insulin injections and food, erratic absorption of insulin, and impaired secretion in some diabetic patients of the so-called counter regulatory hormones such as adrenaline and glucagon that oppose the action of insulin.

About one third of IDDM patients have no warning symptoms of hypoglycaemia (eg sweating, nausea, blurred vision, palpitations) and they rely on intermittent self-monitoring of blood glucose to detect dangerously low glucose levels. The consequences of hypoglycaemia include impaired cognition and consciousness, and eventually coma.

Since the late 1970's, an increasing number of diabetic patients, mostly IDDM, have been measuring their own blood glucose concentrations using finger-prick capillary blood samples. Self blood glucose monitoring (SBGM) is used by diabetics in the home to detect hypoglycaemia or hyperglycaemia and take corrective action such as taking extra food to raise the blood glucose or extra insulin to lower the blood glucose. The measurements, which are made using a low-cost, hand-held blood glucose monitor (BGM), also allow the physician to adjust the insulin dosage at appropriate times so as to maintain near normoglycaemia.

BGMs use either reflectance photometry or an electrochemical method to measure the glucose concentration. Reflectance photometry measures the amount of light reflected from the reagent-impregnated test strip that has reacted with a drop of blood. The operator pricks the finger of the patient or earlobe with a sterile lancet or uses anticoagulated whole blood collected in heparin and then places the blood on the test strip. The operator must place the blood onto the test strip at the time the monitor begins its timing sequence. This step is critical because under-timing (under-incubation) or over-timing (over-incubation) of the reaction may cause inaccurate measurements. At the audible signal, the operator wipes or blots the excess blood off the outside of the test strip. The operator then inserts the strip into the monitor for measurement.

In the electrochemical method a disposable single-use enzyme electrode test strip is used. When the test specimen is placed onto the test strip, an enzymatic reaction occurs that results in a current through the strip. The current is directly proportional to the concentration of glucose in the specimen.

The main disadvantages of SBGM systems are poor patient acceptance because the technique is painful, only intermittent assessment of diabetic control is possible and readings during the night or when the patient is otherwise occupied such as during driving are not possible. It is estimated that less than half of the IDDM patients in the US perform SBGM.

Further, glucose values obtained with BGMs may not agree with clinical laboratory results. Routine laboratory measurements of glucose are performed on either serum of plasma venous blood specimens that correspond with glucose concentrations measured on whole blood glucose analysers.

Whole blood glucose values are lower than those obtained from either serum or plasma. Although glucose is not a static component in human blood, changes in blood glucose concentration following food intake in normal and hyperglycaemic conditions are reasonably predictable. Similarly, the variation in glucose concentration as blood passes from arteries or capillaries to veins has also been documented. Therefore, over time, repeated measurement of blood glucose from the same patient may diverge widely. Also, blood obtained simultaneously by finger stick and venipuncture may not have the same glucose concentration. (Venous blood may contain 1 mmol/l less glucose than capillary blood if the same samples are obtained within 1–2 hours after carbohydrate intake).

Furthermore, the haematocrit of the patient (the volume of cells, mostly erythrocytes, expressed as a percentage of the volume of whole blood in a sample) influences glucose values, and whole blood glucose measurements must be corrected for this. Unfortunately, because BGMs cannot automatically correct for the haematocrit of the patient, an error of 5–15% may be introduced.

There is widespread agreement that for self-monitoring in the home the reluctant acceptance of the current finger-stick method is the main reason why the development of a non-invasive measurement technique has such high priority.

A non-invasive measurement device is known from U.S. Pat. No. 5,553,613. U.S. '613 describes a technique which uses the pulsatile component of the light intensity transmitted through the finger, from which to derive the glucose concentration non-invasively. It does this by using the wavelengths 805 nm, 925 nm, 970 nm and the range 1000–1100 nm. The measurements were made by transmission, ie light was passed through the finger. However, as mentioned above, U.S. '613 specifically relies upon the pulsatile component of the light transmitted through the patient. Such a pulsatile technique has clear disadvantages in that the pulsatile component of the light signal, whether transmitted or reflected, is less than 2% of the total signal. Thus, prior art devices which use only the pulsatile component are much less sensitive and much more vulnerable to patient movement which can cause interference which is in the order of a few hundred times the relevant signal.

Moreover, the pulsatile signal identifies arterial blood specifically. Whilst this is advantageous when considering the pulmonary circulation of a patient, it provides no information on the patient's systemic circulation which is important for glucose determination. Further, pulsatile techniques are limited to use on body extremities, eg finger, ear lobe or the ball of the foot in babies or neo-nates.

International Patent Application No. WO 97/27800 discloses a device for the non-invasive measurement of blood analytes using light transmitted through or reflected from a body part.

However, the invention disclosed in the prior art also suffers from the disadvantage that, inter alia, only the pulsatile element of the transmitted/reflected signal is exploited.

U.S. Pat. No. 5,755,226 describes an apparatus for the non-invasive measurement of blood glucose levels. Furthermore, the disclosed invention does not describe the utilisation of the non-pulsatile element of a patient's blood in the determination of blood analytes.

SUMMARY OF THE INVENTION

The present invention overcomes or mitigates the disadvantages of the prior art by using a plurality of closely associated transmitters and generators which allows an "average" evened out signal to be produced and is capable of utilising the non-pulsatile element of the patient's blood flow. In addition, a further advantage of the invention is that it allows the measurement of oxygen saturation ($SO_2$). Furthermore, the invention permits the measurement of haemoglobin index (HbI) and/or temperature.

According to the invention we provide a device for the non-invasive measurement of one or more analytes in blood in a patient's body part which comprises a light transmitter comprising a plurality of transmitting fibres positioned to transmit light to the body part and a light detector comprising a plurality of light detector fibres position to detect light transmitted through or reflected from the body part.

A preferred embodiment of the invention is one wherein the non-pulsatile element of the patient's blood is utilised.

Thus, according to a further feature of the invention we provide a device for the non-invasive measurement of one or more analytes in blood in a patient's body part as herein before described which is adapted to measure the non-pulsatile element of a patient's blood. In a further preferred embodiment the device measures the pulsatile and non-pulsatile elements of a patient's blood. The device may be so adapted by being provided with a plurality of closely associated transmitters and generators which allows an "average" evened out signal to be produced.

Although various analytes may be measured, the detector of the invention is especially useful in measuring blood glucose level. We especially provide a device for the non-invasive measurement of one or more analytes in blood in a patient's body part as herein before described which is adapted to measure blood glucose levels.

The device may be capable of measuring other parameters either separately or in addition to blood glucose. An especially advantageous feature is the device may be adapted to measure blood oxygen saturation ($SO_2$).

As a further preferred embodiment we provide a device which is adapted to measure the haemoglobin index (HbI) and/or temperature of a patient's blood.

The device may be adapted for use, with any body part although it is preferable that it can be a finger or thumb.

The number or transmitter fibres may vary although we have found that 18 transmitter fibres works well. The number of detector fibres may be the same or different to the number of transmitter fibres, but may vary and we have found that 12 detector fibres works well. The diameter of the detector and the transmitter fibres may be the same or different and may vary, a diameter of 250 $\mu$m is preferred.

The detector fibres are preferably positioned to detect reflected light rather than transmitted light.

The wavelength used in the transmitter fibres will generally be from 500 to 1100 nm. However, it is a further feature of the invention to provide a detector as hereinbefore described which also measures haemoglobin index (HbI) and/or oxygen saturation ($SO_2$) of blood. For such measurement, specific wavelengths are used, namely 500.9 nm, 528.1 nm, 549.5 nm, 561.1 nm, 572.7 nm and 586.3 nm. The preferred wavelengths for measuring blood glucose are from 800 nm to 1100 nm.

According to a further feature of the invention we provide a method of measuring blood glucose levels which comprises placing a non-invasive measuring device as hereinbefore described against a body part of a patient and using the detector to measure the light transmitted through or reflected from the body part.

In a yet further feature of the invention we provide a device according to as herein before described programmed so as to calculate one or more of the haemoglobin index, the oxygen index and the blood oxygen saturation. Clearly, since blood oxygen saturation is dependent upon both the haemoglobin index and the oxygen index, the computer is programmed so as to calculate these equations first if blood oxygen saturation is to be calculated.

We also provide a computer programme product comprising a computer readable medium having thereon computer programme code means, when said programme is loaded, to make the computer execute a procedure to calculate one or more of the haemoglobin index, the oxygen index and the "whole blood" oxygen saturation as herein before described.

The invention will now be illustrated but in no way limited by reference to the following example and drawings in which;

BRIEF DESCRIPTION OF THE DRAWING FIGURES, EXPERIMENTAL DATA AND PREFERRED EMBODIMENTS

Figure 1A:
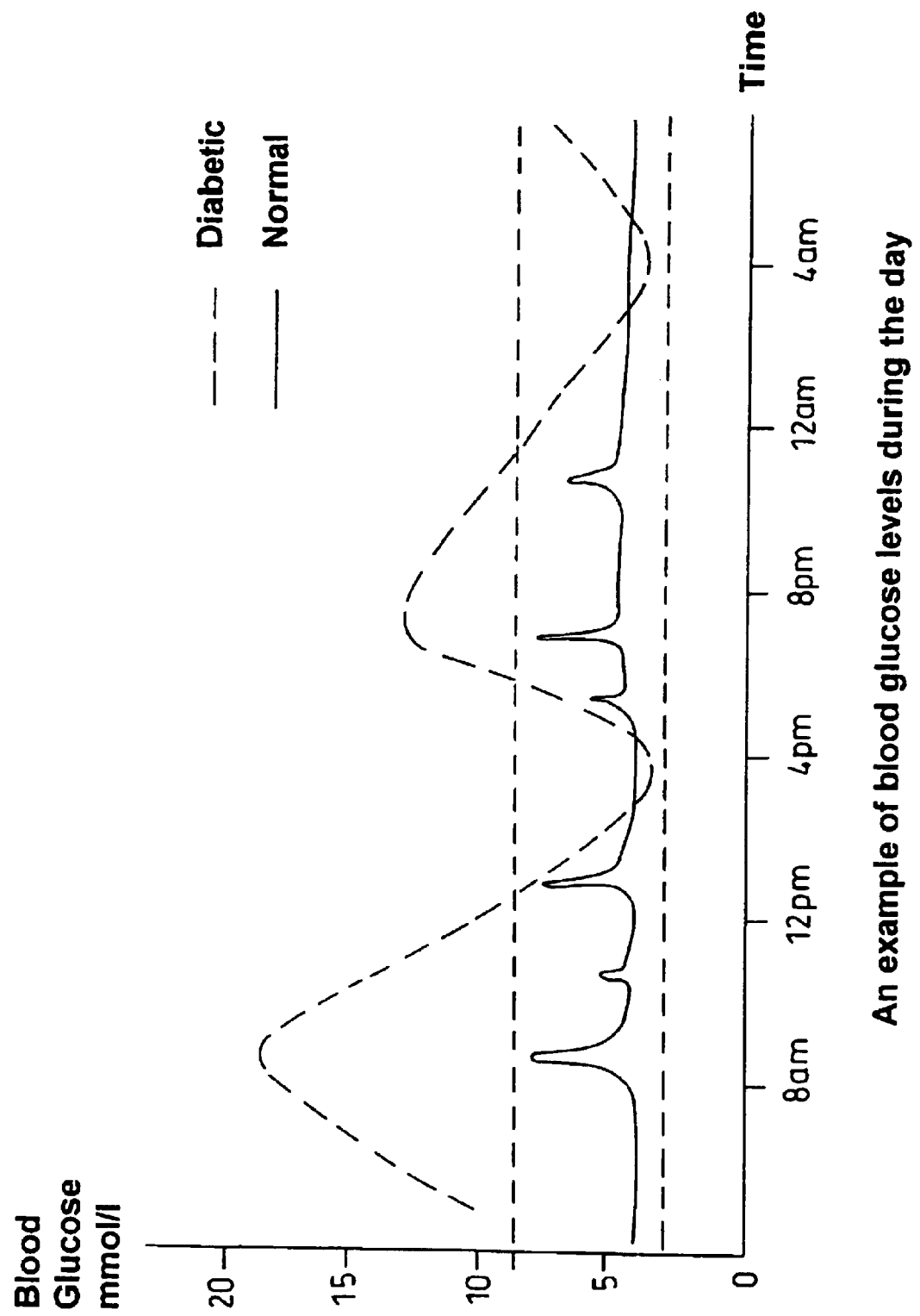

FIG. 1 is a plot of the predicted glucose values against the measured glucose values; and FIG. 1a is a graph comparing normal blood glucose levels with those of a diabetic.

EXAMPLE 1

Glucose measurement

In vivo measurements using the MCPD spectrophotometer were carried out at 10 min intervals on the fingertips of 8 volunteers during the course of glucose tolerance tests and the results compared with those measured using a conventional blood glucose monitor. In addition, parallel measurements of local blood flow (laser Doppler flux) and temperature were made.

The analysis which is presented here uses the same wavelength range used in the previous glucose studies carried out namely: 805 nm, 925 nm, 970 nm and the broadband average 1000–1100 nm, but additionally wavelengths sampled at regular intervals in the entire range 800 nm to 1100 nm. Intervals of 1.96 nm worked well.

Earlier work demonstrated that the glucose-dependent signal emanates from haemoglobin. Furthermore, although the 805 nm wavelength could be used to compensate for small changes in haemoglobin concentration large changes continued to interfere with the sensitivity for glucose. It was furthermore recognised that changes in haemoglobin oxygenation would cause absorption changes from 800 nm to 1100 nm. As in all physiological measurements carried out in the peripheral circulation, temperature is also likely to be a controlling parameter. In the novel analysis carried out on the intensity spectra in the experiments carried out here, the three parameters haemoglobin concentration, oxygen saturation and temperature were introduced into the multiple linear regression analysis along with the near infrared parameters previously used.

Experimental 13 glucose tolerance tests (GTTs) were carried out on 8 different volunteers. In one case, 200 ml water was given instead of the solution of 75 g glucose in 200 ml water; a real GTT was subsequently carried out on the same volunteer. In one volunteer five GTTs were carried out on separate occasions. One volunteer had diabetics.

All measurements were carried out with an Otsuka Optronics Photal MCPD-1000 photodiode array lightguide spectrophotometer. The 0.2 mm slit was used for the diffraction grating giving a full width at half maximum transmission of 7.2 nm, comparable with the glucose monitor. Using the supplied software, the instrument allows access to data points at 1.94 nm intervals within the wavelength range 300–1100 nm. The range displayed during the glucose experiments was 500–1100 nm. In order to mimic the broad bandwidth characteristics of the previous glucose monitor above 1000 nm, all measurements were averaged over the range 1000–1100 nm. Quartz lightguides were used in conjunction with a 400 W quartz-halogen light source.

A lightguide bundle, which consisted of 18 transmitting and 12 receiving fibres each of 250 μm diameter, was attached to the fingertip of the subject by means of a laser Doppler probe holder. Recordings of spectra were made at 10 min intervals throughout the test using the MCPD spectrophotometer described above. These recordings were accompanied by parallel measurements of glucose concentrations in blood, obtained by pinprick of a contralateral finger with the aid of a Softelix pro lancet system, using a Boehringer Manheim Advantage® glucose monitor. The lightguide was removed from the finger after each measurement and new dark and reference spectra recorded before each new measurement. A total of 13 measurements were carried out over a 2 hour period.

Careful selection of integrating time and the intensity of the reference spectrum enabled the simultaneous record of spectra that covered not only the range 800–1100 nm, but also the visible range from 500–600 nm. This enabled the evaluation of skin haemoglobin saturation ($SO_2$) and haemoglobin concentration (HbI) (Harrison D K et al, (1993) *Phys Meas* 14: 241–52) from the same spectra as those being analysed for glucose (see below).

A Moor Instruments DRT4 laser Doppler perfusion monitor was used to measure blood flow changes in the adjacent finger. The probe incorporated a thermal sensor, which was used to measure skin temperature (note: also on the adjacent finger) throughout the experiment.

Derivation of HbI and $SO_2$

HbI and $SO_2$ were derived from the absorption spectra measured from 500.8 to 586.3 nm using a computer program VOXYG written for the purpose. The program carried out the following calculations.

Haemoglobin Index $$HbI=((b-a)/27.1+(c-b)/21.4+(c-e)/23.3+(c-f)/13.6)*100$$

Oxygenation Index $$OXI=(e-d)/11.7-(d-c)/11.6)*100/HbI$$

Oxygen Saturation $$SO_2=100*(OXI+0.43)/1.5$$

where a=absorption value at 500.9 nm
b=absorption value at 528.1 nm
c=absorption value at 549.5 nm
d=absorption value at 561.1 nm
e=absorption value at 572.7 nm
f=absorption value at 586.3 nm

MULTIPLE LINEAR REGRESSION ANALYSIS

A data file A was created containing the full absorption spectral data (800–1100 nm in 1.96 nm steps) from all 12 GTTs in the series. The absorption values in the file are defined in "absorption units" referred to here as ABUs. The other data contained in the file were time, experiment identification, glucose concentration (invasive), HbI, $SO_2$, temperature, and laser Doppler flux.

A number of secondary files were created whereby a sequence of "normalisations" of the data were performed:

B—ABU data of A was normalised by subtraction of the absorption of the values at 802 nm (ie $ABU_A - ABU_{802}$). This is similar to the way in which previous data was treated.

C—ABU data of B was further normalised by division by the HbI value (ie $ABU_B/HbI$). This was designed to take into account of the results of the in vitro experiments which showed that normalisation at, then, 805 nm did not fully compensate for changes in haemoglobin concentration.

D—ABU data of C was further normalised by division by the $SO_2$ value (ie $ABU_C/SO_2$) to take into account the influence of changes in the relative concentrations of oxygenated haemoglobin ($HbO_2$) and deoxygenated haemoglobin (Hb) on the infrared spectrum.

E—SBU data of D was yet further normalised by subtraction of the value at the assumed water peak (ie $ABU_D-ABU_{949}$) in an attempt to take into account changes in water content.

The types and orders of normalisations may vary, and the above are examples.

The above files were then subjected to multiple linear regression, analysis using SPSS for Windows 6.1.2. All of the wavelengths available in the above data files, ie 800 nm to 1100 nm in 1.96 steps were entered as independent variables. The results of the multiple wavelength regressions are given below. The regressions include only the spectral data and not HbI, $SO_2$ or temperature as further independent variables at this stage.

|   | r | Standard Error (SE) (mM) | No of Wavelengths Included |
|---|---|---|---|
| A | 0.48 | 2.81 | 4 |
| B | 0.89 | 1.69 | 37 |
| C | 0.80 | 2.05 | 21 |
| D | 0.89 | 1.61 | 31 |
| E | 0.93 | 1.40 | 48 |

The predicted values from the last correlation using data file E are plotted against the measured glucose values in FIG. 1. The predicted values are given as standardised to the mean and number of standard deviations on the left hand side of the y-axis and as mM on the right hand side.

The results obtained using the multi-wavelength analysis are significant improvements to those using the original parameters applied to the collective results. FIG. 1 could indicate that the method may eventually allow a universal calibration, or at least one based on a particular individual, particularly if the ways in which the spectra are normalised are varied.

Above multiple regression analyses result in regression equations whose coefficients can be incorporated into an equation to produce a new parameter "calculated Glucose". This, together with the parameters HbI, $SO_2$ and temperature can then be incorporated into a further regression equation for each individual GTT.

Least squares fitting of mean "calibration spectra" recorded from the GTT series could be used for a universal or individual calibration.

What is claimed is:

1. An apparatus for measuring hemoglobin index (HbI) in blood of a patient, comprising:
   a light source generating broadband light;
   a light-transmission arrangement including a plurality of transmitting fibers positioned for simultaneously transmitting multiple wavelengths of said broadband light from said light source to the blood of the patient;
   an optical fiber arrangement having a plurality of light detector fibers for leading multi-wavelength light, in spectrally unseparated form, transmitted through, or reflected from, the blood;
   a light detection arrangement receiving said multi-wavelength light in its spectrally unseparated form from said optical fiber arrangement, for spectrally decomposing the received light, and for determining amplitudes of selected wavelengths of the decomposed light; and,
   means for utilizing a non-pulsatile element of the blood of the patient for determining a measurement of the hemoglobin index (HbI) in the blood as a function of the amplitudes of the selected wavelengths.

2. The apparatus for measuring hemoglobin index (HbI) in blood of a patient according to claim 1, further comprising means for utilizing a pulsatile element of the blood of the patient for determining the measurement of at least one analyte in the blood.

3. The apparatus for measuring hemoglobin index (HbI) in blood of a patient according to claim 1, further comprising a plurality of closely associated transmitters and generators for providing an "average-evened out" signal to be produced for representing the measurement of at least one analyte in the blood.

4. The apparatus for measuring hemoglobin index (HbI) in blood of a patient according to claim 1, wherein said apparatus is capable of measuring blood glucose level.

5. The apparatus for measuring hemoglobin index (HbI) in blood of a patient according to claim 1, wherein said apparatus is capable of measuring blood oxygen saturation ($SO_2$).

6. The apparatus for measuring hemoglobin index (HbI) in blood of a patient according to claim 1, further comprising means for measuring temperature of the blood of the patient.

7. The apparatus for measuring hemoglobin index (HbI) in blood of a patient according to claim 1, wherein said apparatus is capable of measuring at least two analytes in the blood of a patient, with one analyte of said at least two analytes being hemoglobin index (HbI) and at least one additional analyte being selected from blood glucose level, blood oxygen saturation ($SO_2$), and temperature of the blood of the patient.

8. The apparatus for measuring hemoglobin index (HbI) in blood of a patient according to claim 7, wherein said apparatus is capable of measuring at least two analytes in the blood of the patient via a computer program.

9. The apparatus for a measuring hemoglobin index (HbI) in blood of a patient according to claim 8, wherein said computer program conducts a multiple linear regression analysis on spectral data collected by said plurality of light detector fibers.

10. The apparatus for measuring hemoglobin index (HbI) in blood of a patient according to claim 7, wherein said apparatus is capable of measuring each of blood glucose level, blood oxygen saturation ($SO_2$), hemoglobin index (HbI) and temperature of the blood of the patient.

11. The apparatus for measuring hemoglobin index (HbI) in blood of a patient according to claim 1, wherein said apparatus includes a greater number of said transmitting fibers than said light detector fibers.

12. The apparatus for measuring hemoglobin index (HbI) in blood of patient according to claim 1, wherein said light detector includes 6 through 18 of said light detector fibers.

13. The apparatus for measuring hemoglobin index (HbI) in blood of a patient according to claim 12, wherein said light detector includes 12 of said detector fibers.

14. The apparatus for measuring hemoglobin index (HbI) in blood of patient according to claim 1, wherein said light detector fibers and said transmitting fibers each have diameters of from 200 to 300 microns.

15. The apparatus for measuring hemoglobin index (HbI) in blood of patient according to claim 1, wherein said light detector fibers are positioned for detecting transmitted light rather than reflected light.

16. The apparatus for measuring hemoglobin index (HbI) in blood of a patient according to claim 1, wherein said light source generates light over a spectrum including a wavelength region of from 500 to 1,100 nm.

17. The apparatus for measuring hemoglobin index (HbI) in blood of a patient according to claim 16, wherein said source generates light over a spectrum including said wavelength region of from 800 to 1,100 nm.

18. The apparatus for measuring hemoglobin index (HbI) in blood of a patient according to claim 16, wherein said multiple wavelengths of said broadband light from said light source include the wavelengths of 500.9 nm, 528.1 nm, 549.5 nm, 561.1 nm, 572.7 nm and 586.3 nm and from 800 to 1,100 nm.

19. The apparatus for measuring hemoglobin index (HbI) in blood of a patient according to claim 1, wherein said multiple wavelengths of said broadband light from said light source include the wavelengths of 500.9 nm, 528.1 nm, 549.5 nm, 561.1 nm, 572.7 nm and 586.3 nm.

20. A method for measuring blood oxygen saturation in blood of a patient, comprising the steps of:

placing against a body part of a patient an apparatus for a non-invasive measurement of at least one analyte in blood in a body part of a patient, said apparatus comprising:

a light transmitter having a plurality of transmitting fibers positioned for transmitting light to the body part of the patient;

a light detector having a plurality of light detector fibers for detecting light transmitted through, or reflected from, the body part of the patient;

means for utilizing a non-pulsatile element of the blood in the body part of the patient for determining a measurement of at least one analyte in the blood; and, means for measuring blood oxygen saturation ($SO_2$), said means for measuring blood oxygen saturation ($SO_2$) including calculation means using the equation:

$$SO_2 = 100 \cdot (OXI + 0.43)/1.5$$

wherein,

OXI is the oxygenation index of the blood of the patient and is defined by the equation:

$$OXI = (e-d)/11.7 - (d-c)/11.6) \cdot 100/HbI,$$

wherein,

HbI is the hemoglobin index of the blood of the patient and is defined by the equation:

$$HbI = ((b-a)/27.1 + (c-b)/21.4 + (c-e)/23.3 + (c-f)/13.6) \cdot 100,$$

and wherein, a=absorption value at 500.9 nm wavelength of light;
b=absorption value at 528.1 nm wavelength of light;
c=absorption value at 549.5 nm wavelength of light;
d=absorption value of 561.1 nm wavelength of light;
e=absorption value of 572.7 nm wavelength of light; and,
f=absorption value of 586.3 nm wavelength of light;
and, utilizing said light detector of said apparatus for measuring light transmitted through, or reflected from, the body part of the patient.

21. A computer program for measuring one or more of the hemoglobin index, the oxygenation index or the blood oxygen saturation level in blood of a patient, comprising:

a computer readable medium having computer program code means on said computer readable medium, said computer program code means calculating one or more of the following equations:

HbI is the hemoglobin index of the blood of the patient and is defined by the equation:

$$HbI = ((b-a)/27.1 + (c-b)/21.4 + (c-e)/23.3 + (c-f)/13.6) \cdot 100,$$

wherein, a=absorption value at 500.9 nm wavelength of light;
b=absorption value at 528.1 nm wavelength of light;
c=absorption value at 549.5 nm wavelength of light;
d=absorption value of 561.1 nm wavelength of light;
e=absorption value of 572.7 nm wavelength of light; and,
f=absorption value of 586.3 nm wavelength of light;

OXI is the oxygenation index of the blood of the patient and is defined by the equation:

$$OXI = [(e-d)/11.7 - (d-c)/11.6] \cdot 100/HbI; \text{ and,}$$

$SO_2$ is the blood oxygen saturation of the blood of the patient and is defined by the equation:

$$SO_2 = 100 \cdot (OXI + 0.43)/1.5.$$

22. An apparatus for a non-invasive measurement of at least one analyte in blood in a body part of a patient, comprising:

a light transmitter having a plurality of transmitting fibers positioned for transmitting light to the body part of the patient;

a light detector having a plurality of light detector fibers for detecting light transmitted through, or reflected from, the body part of the patient; and, means for utilizing a non-pulsatile element of the blood in the body part of the patient for determining a measurement of at least one analyte in the blood, said measurement of said at least one analyte including means for measuring blood oxygen saturation ($SO_2$) using the equation:

$$SO_2 = 100 \cdot (OXI + 0.43)/1.5,$$

wherein,

OXI is the oxygenation index of the blood of the patient and is defined by the equation:

$$OXI = [(e-d)/11.7 - (d-c)/11.6] \cdot 100/HbI,$$

wherein,

HbI is the hemoglobin index of the blood of the patient and is defined by the equation:

$$HbI = [(b-a)/27.1 + (c-b)/21.4 + (c-e)/23.3 + (c-f)/13.6] \cdot 100,$$

wherein, a=absorption value at 500.9 nm wavelength of light;
b=absorption value at 528.1 nm wavelength of light;
c=absorption value at 549.5 nm wavelength of light;
d=absorption value of 561.1 nm wavelength of light;
e=absorption value of 572.7 nm wavelength of light; and,
f=absorption value of 586.3 nm wavelength of light.

23. An apparatus for a non-invasive measurement of at least one analyte in blood in a body part of a patient, comprising:
- a light transmitter having a plurality of transmitting fibers positioned for transmitting light to the body part of the patient;
- a light detector having a plurality of light detector fibers for detected light transmitted through, or reflected from, the body part of the patient; and,
- means for utilizing a non-pulsatile element of the blood in the body part of the patient for determining a measurement of at least one analyte in the blood, said measurement of said at least one analyte including means for measuring the hemoglobin index (HbI) includes calculation means using the equation:

$$HbI=[(b-a)/27.1+(c-b)/21.4+(c-e)/23.3+(c-f)/13.6]\cdot 100,$$

wherein, a = absorption value at 500.9 nm wavelength of light;

b = absorption value at 528.1 nm wavelength of light;

c = absorption value at 549.5 nm wavelength of light;

d = absorption value of 561.1 nm wavelength of light;

e = absorption value of 572.7 nm wavelength of light; and, f = absorption value of 586.3 nm wavelength of light.

* * * * *

UNITED STATES PATENT AND TRADEMARK OFFICE
CERTIFICATE OF CORRECTION

| | | |
|---|---|---|
| PATENT NO. | : 6,990,365 B1 | Page 1 of 1 |
| APPLICATION NO. | : 09/743206 | |
| DATED | : January 24, 2006 | |
| INVENTOR(S) | : Dawood Parker et al. | |

It is certified that error appears in the above-identified patent and that said Letters Patent is hereby corrected as shown below:

On the title page, item [73];

The Assignee should read:

Whitland Research Limited, Carms, United Kingdom

Signed and Sealed this
Twenty-sixth Day of July, 2011

David J. Kappos
*Director of the United States Patent and Trademark Office*